United States Patent
Yamanaka et al.

(10) Patent No.: US 11,258,047 B2
(45) Date of Patent: Feb. 22, 2022

(54) ORGANIC ELECTROLUMINESCENT ELEMENT AND MEASUREMENT APPARATUS

(71) Applicant: HAMAMATSU PHOTONICS K.K., Hamamatsu (JP)

(72) Inventors: Takahiko Yamanaka, Hamamatsu (JP); Shigeo Hara, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 155 days.

(21) Appl. No.: 16/823,886

(22) Filed: Mar. 19, 2020

(65) Prior Publication Data
US 2020/0313120 A1    Oct. 1, 2020

(30) Foreign Application Priority Data
Mar. 26, 2019    (JP) .............................. JP2019-058867

(51) Int. Cl.
*H01L 51/52*    (2006.01)
*A61B 5/00*    (2006.01)
*G01J 3/28*    (2006.01)

(52) U.S. Cl.
CPC ........ *H01L 51/5271* (2013.01); *A61B 5/0071* (2013.01); *A61B 5/0075* (2013.01); *G01J 3/28* (2013.01); *H01L 51/5206* (2013.01); *H01L 51/5221* (2013.01); *H01L 51/5284* (2013.01)

(58) Field of Classification Search
CPC ..... H01L 51/5271; H01L 51/5284; G01J 3/28
See application file for complete search history.

(56) References Cited

U.S. PATENT DOCUMENTS

2020/0168668 A1*    5/2020    Kim .................... H01L 51/5271

FOREIGN PATENT DOCUMENTS

| JP | S63-046000 U | 3/1988 |
|---|---|---|
| JP | 2013-010314 A | 1/2013 |
| JP | 2013-011804 A | 1/2013 |
| JP | 2013-011805 A | 1/2013 |

\* cited by examiner

*Primary Examiner* — Anthony Ho
(74) *Attorney, Agent, or Firm* — Faegre Drinker Biddle & Reath LLP

(57) ABSTRACT

An organic EL element 100 includes a light emitting layer 110 containing an organic light emitting material, a light shielding electrode 120 being arranged on one surface 110$a$ side of the light emitting layer 110, a light transmissive electrode 130 being arranged on the other surface 110$b$ side of the light emitting layer 110, a reflection filter 160 being arranged on a side opposite to the light emitting layer 110 with respect to the light transmissive electrode 130 and selectively reflecting a light L1 from the light emitting layer 110.

15 Claims, 13 Drawing Sheets

ORGANIC ELECTROLUMINESCENT ELEMENT AND MEASUREMENT APPARATUS

TECHNICAL FIELD

The present invention relates to an organic electroluminescent element and a measurement apparatus.

BACKGROUND

In the related art, various light emitting elements have been proposed regardless of the intended use (refer to, for example, Japanese Unexamined Utility Model Publication No. S63-46000), and the light emitting elements can be used as measurement apparatuses such as a living body measurement apparatus that performs living body sensing. For example, with respect to the living body sensing, light in all wavelength bands is absorbed in the living body due to the fact that many substances are contained in the living body, but near-infrared light (light in the near infrared range) is difficult to be absorbed in the living body as compared with light in the other wavelength bands. For this reason, the living body sensing can be performed by using the near-infrared light. Specifically, in a state where a measurement apparatus including a light emitting element that emits near-infrared light and a light detector is placed in close contact with an epidermis of the living body, an interior of the living body is irradiated with the light from the light emitting element, and then, the light scattered from the interior of the living body is detected with the detector.

SUMMARY

In the living body sensing, there is a case where it is required to evaluate spectral intensities (peak intensities) of a plurality of emission spectra with a narrowed spectral width (peak width). In this case, it is considered to narrow the spectral width of the broad emission spectrum with an optical filter, and for example, in a light emitting element disclosed in Japanese Unexamined Utility Model Publication No. S63-46000, the light emitting element using a light transmission filter (transparent resin film) having a light coloring filter function has been proposed.

On the other hand, from the viewpoint of performing various measurements, it is desirable that the degree of freedom of optical layouts in the measurement apparatus is high. However, when a light transmission filter is used as in the light emitting element disclosed in Japanese Unexamined Utility Model Publication No. S63-46000, even if the spectral width can be narrowed, the light emission direction is uniquely limited by the structure of the element, and thus, it is difficult to achieve various optical layouts.

An aspect of the present invention is to solve the above-described problems and is to provide an organic electroluminescent element capable of achieving various optical layouts while narrowing a spectral width. In addition, another aspect of the present invention is to provide a measurement apparatus including the organic electroluminescent element.

One aspect of the present invention provides an organic electroluminescent element including: a light emitting layer containing an organic light emitting material; a first electrode having a light shielding property, the first electrode being arranged on one surface side of the light emitting layer; a second electrode having a light transmitting property, the second electrode being arranged on the other surface side of the light emitting layer; and a reflection filter being arranged on a side opposite to the light emitting layer with respect to the second electrode and selectively reflecting light from the light emitting layer.

Another aspect of the present invention provides a measurement apparatus including the above-described organic electroluminescent element and a light detector.

According to such an organic electroluminescent element and measurement apparatus, in the organic electroluminescent element, the light from the light emitting layer is transmitted through the second electrode having a light transmitting property and selectively reflected by the reflection filter. In this case, by using the reflection filter selectively reflecting a light component having a desired wavelength, a light component having a narrowed spectral width can be emitted from the organic electroluminescent element. In addition, by adjusting the light emission direction of the light emitting layer, the relative position between the light emitting layer and the reflection filter, the reflection position and the reflection angle of the reflection filter, or the like, the light reflected by the reflection filter can be emitted in a desired direction, so that it is possible to achieve various optical layouts.

According to one aspect of the present invention, it is possible to provide an organic electroluminescent element capable of achieving various optical layouts while narrowing a spectral width. In addition, according to another aspect of the present invention, it is possible to provide a measurement apparatus including the organic electroluminescent element. According to another aspect of the present invention, it is possible to provide applications of an organic electroluminescent element and a measurement apparatus to living body sensing.

DETAILED DESCRIPTION

Figure 1:
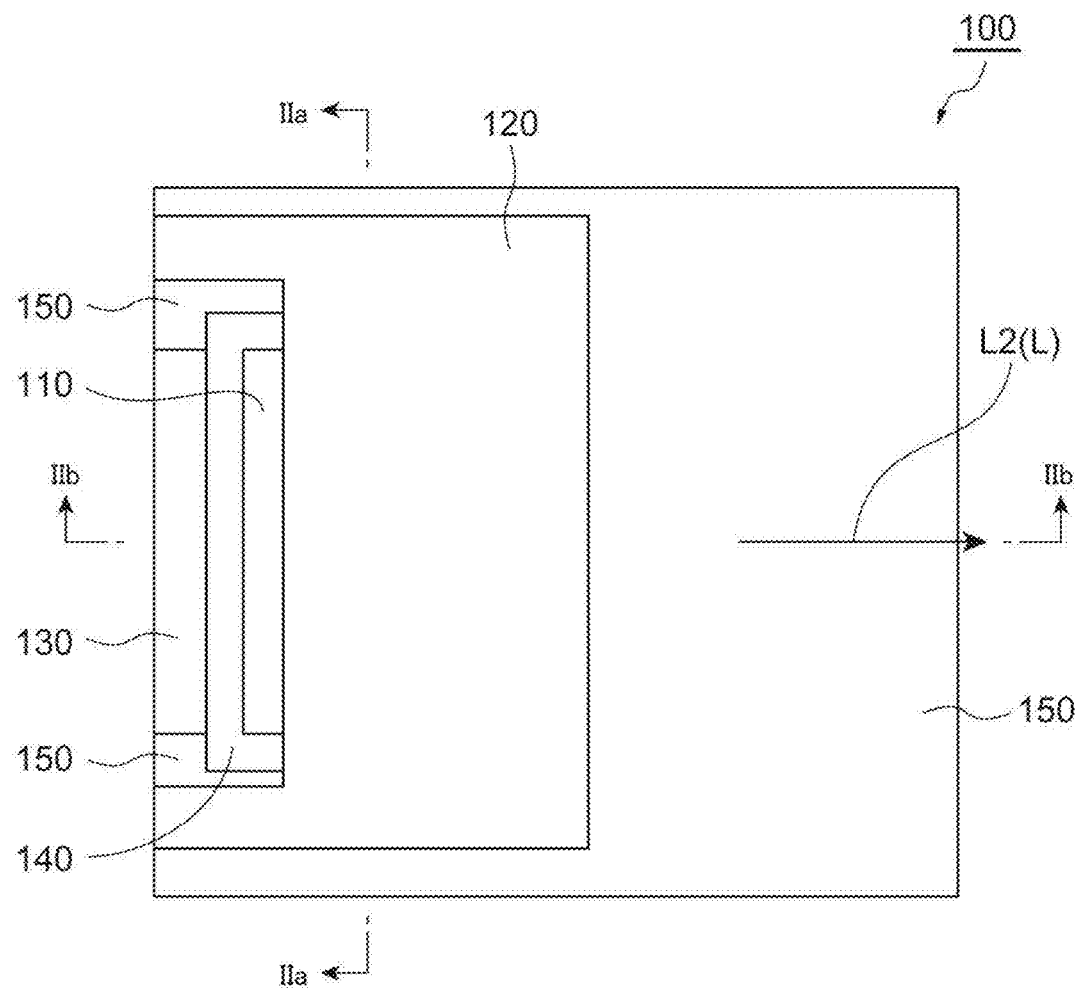
FIG. 1 is a schematic plan view illustrating an organic electroluminescent element of a first embodiment.

Hereinafter, embodiments of the present invention will be described with reference to the drawings as appropriate. In each drawing, the same elements are denoted by the same reference numerals, and in some cases, overlapping description is omitted. In the drawings, in some cases, a perpendicular coordinate system S defined by an X axis, a Y axis, and a Z axis perpendicular to each other is illustrated. In the drawings, lights before and after being reflected by a reflection filter are collectively illustrated as a light L. In the present specification, examples of a near-infrared light include a light having a wavelength of 700 to 2500 nm.

Figure 2A:
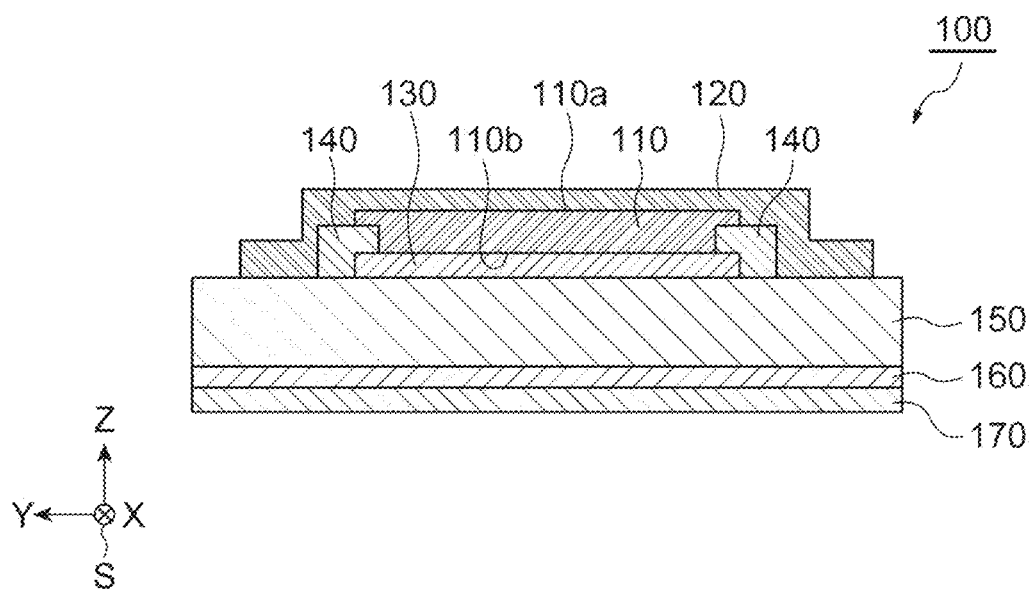
FIG. 2A is a cross-sectional view taken along line IIa-IIa in FIG. 1.
Figure 2B:
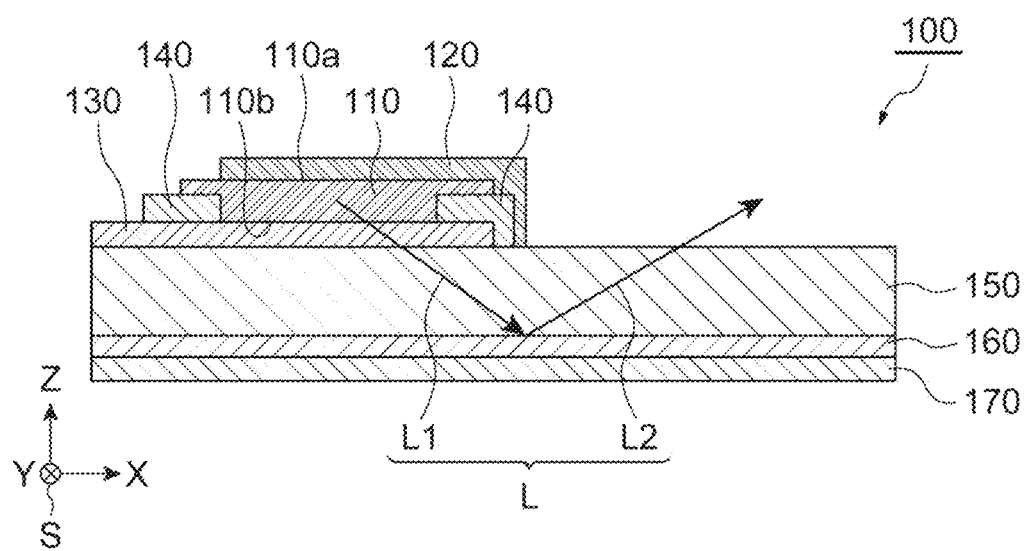
FIG. 2B is a cross-sectional view taken along line IIb-IIb in FIG. 1.

FIG. 1 is a schematic plan view illustrating an organic electroluminescent element (organic light emitting element; hereinafter also referred to as an "organic EL element") of a first embodiment. FIG. 2A is a cross-sectional view taken along line IIa-IIa in FIG. 1, and FIG. 2B is a cross-sectional view taken along line IIb-IIb in FIG. 1. An organic EL element 100 in FIG. 1, FIG. 2A and FIG. 2B includes a light emitting layer 110, a light shielding electrode (the first electrode having a light shielding property) 120, a light transmissive electrode (the second electrode having a light transmitting property) 130, an insulating layer 140, a light transmissive substrate 150, a reflection filter 160, and a light absorbing member (light absorber) 170.

The light absorbing member 170, the reflection filter 160, the light transmissive substrate 150, the light transmissive electrode 130, the light emitting layer 110, and a portion of the light shielding electrode 120 are laminated in this order, and the lamination direction corresponds to the Z-axis direction of the perpendicular coordinate system S. The remaining portion of the light shielding electrode 120 and the insulating layer 140 are arranged outside the light emitting layer 110 and the light transmissive electrode 130 on the light transmissive substrate 150. The light L1 emitted from the light emitting layer 110 is transmitted through the light transmissive electrode 130 and the light transmissive substrate 150 and then is reflected by the reflection filter 160, and the reflected light L2 travels in the XZ plane of the perpendicular coordinate system S. The organic EL element 100 has a rectangular shape in the XY plane.

The light emitting layer 110 is arranged between the light shielding electrode 120 and the light transmissive electrode 130. The light emitting layer 110 has a rectangular shape in the XY plane. The light emitting layer 110 is arranged in a region extending from the center of the organic EL element 100 to the vicinity of the end portion (left end portion in the drawing) on the negative X-axis direction side in the XY plane. The light emitting layer 110 has one surface 110a and the other surface 110b facing each other in the Z-axis direction.

The light emitting layer 110 emits the light L1 in the arrangement direction (the negative Z-axis direction) of the reflection filter 160 with respect to the light emitting layer 110 and irradiates the reflection filter 160 with the light L1. The light emitting layer 110 may emit lights in a direction other than the arrangement direction of the reflection filter 160 and may emit lights, for example, in the arrangement direction (the positive Z-axis direction) of the light shielding electrode 120 with respect to the light emitting layer 110. For example, the light emitting layer 110 can emit lights including near-infrared light. The thickness of the light emitting layer 110 is, for example, 10 to 500 nm.

The light emitting layer 110 may be a layer that excitons are generated by recombination of electrons and holes injected from the light shielding electrode 120 and the light transmissive electrode 130 and then emits lights. The electrons and the holes may be injected from any one of the light shielding electrode 120 and the light transmissive electrode 130.

The light emitting layer 110 contains an organic light emitting material, a host material, and the like. Examples of the organic light emitting material include a phosphorescent material, a delayed fluorescent material, and a fluorescent material (excluding the delayed fluorescent material). The delayed fluorescent material may be an organic compound that can reverse intersystem cross to the excited singlet state after transitioning to the excited triplet state and emits fluorescence when returning from the excited singlet state to the ground state. The fluorescent material may be an organic compound that emits fluorescence when returning from the excited singlet state to the ground state although the organic compound substantially cannot reverse intersystem cross unlike the delayed fluorescent material.

The host material can disperse the organic light emitting material. The host material may be an organic compound that confines at least triplet energy of the phosphorescent material or the delayed fluorescent material in the light emitting layer 110. The light emitting layer 110 may contain three components of the delayed fluorescent material, the fluorescent material, and the host material and may have a configuration of using energy transfer from the delayed fluorescent material to the fluorescent material.

The light shielding electrode 120 is arranged on the one surface 110a side of the light emitting layer 110 and is in contact with the light emitting layer 110. More specifically, the light shielding electrode 120 includes a first electrode portion which is arranged on the one surface 110a side of the light emitting layer 110 and a second electrode portion which is arranged outside the first electrode portion, the light emitting layer 110, the light transmissive electrode 130 and the insulating layer 140 on the light transmissive substrate 150 and connected to the first electrode portion. The first electrode portion of the light shielding electrode 120 has a rectangular shape in the XY plane. The first electrode portion is arranged in a region extending from the center of the organic EL element 100 to the end portion on the negative X-axis direction side in the XY plane, and has an opening through which the light emitting layer 110, the light transmissive electrode 130, the insulating layer 140, and a portion of the light transmissive substrate 150, which are arranged in the lower layer, are exposed on this end portion side. The second electrode portion of the light shielding electrode 120 includes a pair of portions extending in the X-axis direction and a portion extending in the Y-axis direction and is arranged around the light emitting layer 110, the light transmissive electrode 130, and the insulating layer 140 except for the end portion side of the organic EL element 100 on the negative X-axis direction side. The second electrode portion is arranged around the light emitting layer 110, so that the light that is not irradiated on the reflection filter 160 is suppressed from being emitted to the outside of the organic EL element 100.

The light shielding electrode 120 is a light shielding (light non-transmissive) electrode and shields (prevents transmission of) a portion or all of the light L1 from the light emitting layer 110. The light shielding electrode 120 may be a light reflective electrode and may reflect light from the light emitting layer 110. The light shielding electrode 120 may be a light absorbing electrode and may absorb light from the light emitting layer 110. The thickness (the thickness of the first electrode portion) of the light shielding electrode 120 is, for example, 10 to 5000 nm.

The light transmissive electrode 130 is arranged on the other surface 110b side of the light emitting layer 110 and is in contact with the light emitting layer 110. The light transmissive electrode 130 is arranged on the light transmissive substrate 150 and is in contact with the light transmissive substrate 150. The light transmissive electrode 130 has a rectangular shape in the XY plane. The light transmissive electrode 130 is arranged in a region extending from the center of the organic EL element 100 to the end portion on the negative X-axis direction side in the XY plane. The light transmissive electrode 130 can transmit a portion or all of the light L1 from the light emitting layer 110. The thickness of the light transmissive electrode 130 is, for example, 10 to 1000 nm.

The light transmissive electrode 130 may be an electrode having a gap through which light travels straight and penetrates (transmits) from one surface to the other surface of the light transmissive electrode 130 and may be, for example, a mesh electrode. The light transmissive electrode 130 may not have a gap through which light travels straight and penetrates from one surface to the other surface of the light transmissive electrode 130 and may be an electrode other than the mesh electrode. For example, the light transmissive electrode 130 may be an electrode through which light can be optically transmitted or may be a solid electrode made of an organic material, an inorganic material, or the like.

The light shielding electrode 120 and the light transmissive electrode 130 have a conductive property and are a cathode and an anode, respectively. The light shielding electrode 120 and the light transmissive electrode 130 may be configured as an anode and a cathode, respectively. Examples of the method for forming an electrode include a method of patterning a thin film formed by vapor deposition, sputtering or the like of an electrode material, a method of performing vapor deposition, sputtering or the like of an electrode material through a mask, and a wet film formation method such as a printing method or a coating method.

As an electrode material constituting the anode, a metal, an alloy, an electrically conductive compound, a mixture thereof, or the like having a high work function (for example, 4 eV or more) can be used. Specific examples of the electrode material include a metal such as Au; CuI, ITO (indium oxide-tin oxide based oxide), IZO (indium oxide-zinc oxide based oxide), $SnO_2$, and ZnO.

As an electrode material constituting the cathode, a metal, an alloy, an electrically conductive compound, a mixture thereof, or the like having a low work function (for example, 4 eV or less) can be used. Specific examples of the electrode material include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal.

The insulating layer 140 is arranged for the purpose of, for example, suppressing contact between the light shielding electrode 120 and the light transmissive electrode 130. The insulating layer 140 includes a portion on the light transmissive substrate 150 which is arranged around the light transmissive electrode 130 except for the end portion side on the negative X-axis direction side and a portion on the light transmissive electrode 130 which has an opening for allowing the light emitting layer 110 and the light transmissive electrode 130 to be contact with each other. Examples of the insulating material constituting the insulating layer 140 include an acrylic resin, polyimide, an epoxy resin, a novolac resin, and silicon oxide (for example, $SiO_2$).

The light transmissive substrate 150 supports the light emitting layer 110, the light shielding electrode 120, the light transmissive electrode 130, and the insulating layer 140 and is in contact with the light shielding electrode 120, the light transmissive electrode 130, and the insulating layer 140. The light transmissive substrate 150 is arranged between the light transmissive electrode 130 and the reflection filter 160. The light transmissive substrate 150 has a rectangular shape in the XY plane. The thickness of the light transmissive substrate 150 is, for example, 0.001 to 10 mm. Examples of the material constituting the light transmissive substrate 150 include a glass, transparent plastic, and quartz. The material constituting the light transmissive substrate 150 may be a flexible material such as polyethylene terephthalate (PET), polyethylene naphthalate (PEN), polyimide, or a glass film from the viewpoint of easy improvement of flexibility.

The reflection filter 160 is arranged on the side opposite to the light emitting layer 110 with respect to the light transmissive electrode 130 and is arranged on the side opposite to the light emitting layer 110 with respect to the light transmissive substrate 150. The reflection filter 160 is in contact with the light transmissive substrate 150. The light transmissive substrate 150 is interposed between the light transmissive electrode 130 and the reflection filter 160, so that the light transmissive electrode 130 and the reflection filter 160 are not in contact with each other.

The reflection filter 160 selectively reflects the light L1 from the light emitting layer 110 and allows the reflected light L2 to travel in the light emission direction. By adjusting the filter used as the reflection filter 160, it is possible to extract the reflected light L2 having a desired wavelength, and it is possible to allow the reflected light L2 to travel in a desired light emission direction. The reflected light L2 contains a light component having a peak wavelength in the range of, for example, 400 to 2500 mm. The reflection filter 160 has a rectangular shape in the XY plane. The thickness of the reflection filter 160 is, for example, 0.001 to 1 mm. Examples of the material constituting the reflection filter 160 include titanium oxide, tantalum oxide, silicon oxide, and magnesium fluoride. The material constituting the reflection filter 160 may be a flexible material such as a polymer material (for example, a resin material) from the viewpoint of easy improvement of flexibility.

As the polymer material, a homopolymer of a single monomer, a copolymer of a plurality of monomers, or the like can be used. As the copolymer, a block copolymer, a random copolymer, a graft copolymer, or the like can be used. Examples of the block copolymer include a binary block copolymer such as polystyrene-b-poly(methylmethacrylate), polystyrene-b-poly(ethylmethacrylate), polystyrene-b-poly(propylmethacrylate), polystyrene-b-poly(tert-butylmethacrylate), polystyrene-b-poly(n-butylmethacrylate), polystyrene-b-poly(isopropylmethacrylate), polystyrene-b-poly(pentylmethacrylate), polystyrene-b-poly(hexylmethacrylate), polystyrene-b-poly(decylmethacrylate), polystyrene-b-poly(dodecylmethacrylate), polystyrene-b-poly(methylacrylate), polystyrene-b-poly(tert-butylacrylate), polystyrene-b-polybutadiene, polystyrene-b-polyisoprene, polystyrene-b-polydimethylsiloxane, polybutadiene-b-polydimethylsiloxane, polyisoprene-b-polydimethylsiloxane, polyvinylpyridine-b-poly(methylmethacrylate), polyvinylpyridine-b-poly(tert-butylmethacrylate), polyvinylpyridine-b-polybutadiene, polyvinylpyridine-b-isoprene, polybutadiene-b-polyvinylnaphthalene, polyvinylnaphthalene-b-poly(methylmethacrylate), and polyvinylnaphthalene-b-poly(tert-butylmethacrylate); a ternary block copolymer such as polystyrene-b-polybutadiene-b-poly(methylmethacrylate), polystyrene-b-polybutadiene-b-poly(tert-butylmethacrylate), polystyrene-b-polyisoprene-b-poly(methylmethacrylate), and polystyrene-b-polyisoprene-b-poly(tert-butylmethacrylate).

The reflection filter 160 may be a polymer filter (a filter made of a polymer material). As the polymer filter, a filter which selectively reflects a desired light component and includes a resin layer having a microphase separation structure containing a block copolymer and including a lamellar-shaped micro domain can be used. The micro domain may have a wave shape having an amplitude in the thickness direction of the filter. In the micro domain, the maximum value of the distance in the thickness direction between the top of the convex portion and the bottom of the concave portion of the micro domain may be larger than the wavelength in the visible light region. The polymer filter may include a plurality of the resin layers described above. The polymer filter may be in a mode where, in the micro domain of one resin layer, the maximum value of the distance in the thickness direction between the top of the convex portion and the bottom of the concave portion of the micro domain is larger than a wavelength in the visible light region, and in the micro domain of the other resin layer, the distance in the thickness direction between the top of the convex portion and the bottom of the concave portion of the micro domain is equal to or smaller than a wavelength in the visible light region. As the polymer filter, films described in Japanese Unexamined Patent Publication Nos. 2013-011804, 2013-010314, 2013-011805, and the like can be used.

Figure 3:
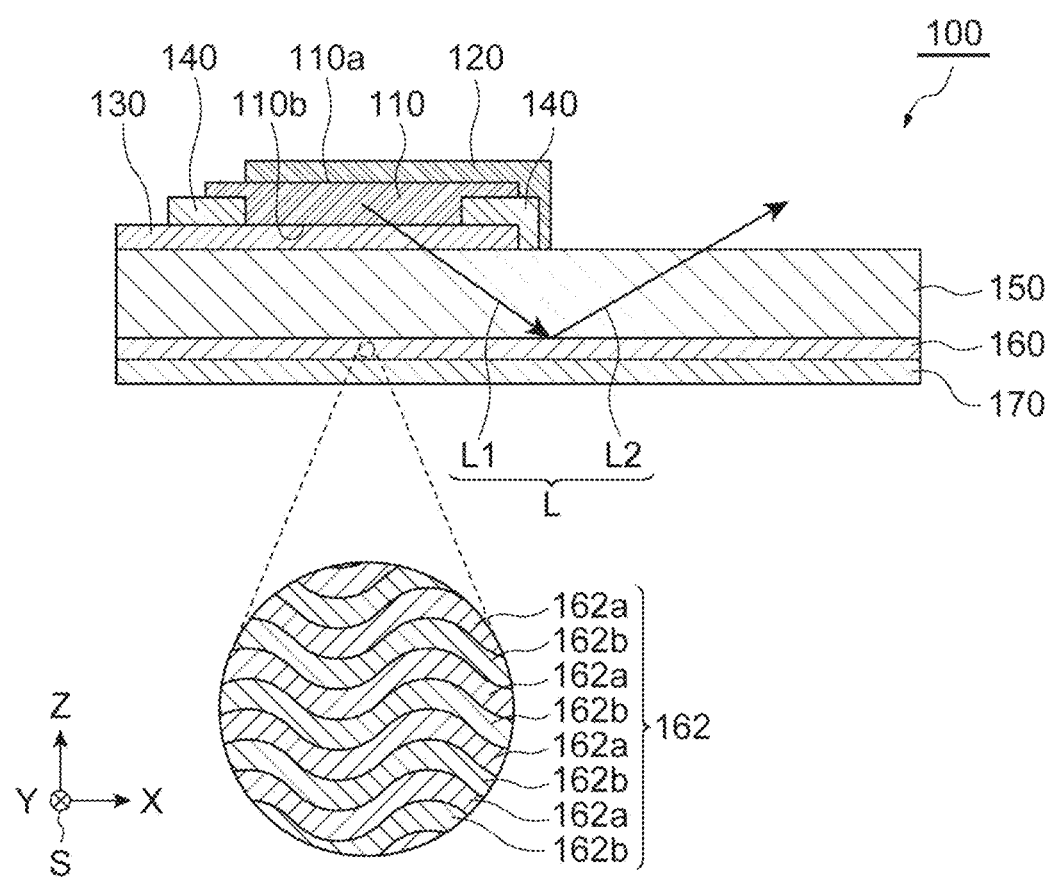
FIG. 3 is a cross-sectional view for describing an example of a reflection filter.

FIG. 3 is a cross-sectional view for describing an example of the reflection filter. The reflection filter 160 in FIG. 3 is a resin layer having a microphase separation structure containing a block copolymer and including a lamellar-shaped micro domain. The microphase separation structure includes a lamellar-shaped micro domain 162 including micro domain 162a and micro domain 162b and is a refractive-index periodic structure formed by alternately laminating the micro domain 162a and the micro domain 162b. The micro domain 162a contains, for example, one polymer chain of the block copolymer as a main component, and the micro domain 162b contains another polymer chain of the block copolymer as a main component.

The light absorbing member 170 includes a light absorbing portion located on the side opposite to the light emitting layer 110 with respect to the reflection filter 160. In the organic EL element 100, the light absorbing member 170 is composed of the light absorbing portion. The light absorbing member 170 is in contact with the reflection filter 160. The light absorbing member 170 can absorb a portion or all of the light components transmitted through the reflection filter 160 among the light L1 from the light emitting layer 110. The light absorbing member 170 has a rectangular shape in the XY plane. The light absorbing member 170 (light absorbing portion) has, for example, a layered shape. The thickness of the light absorbing member 170 is, for example, 0.001 to 1 mm. Examples of the material constituting the light absorbing member 170 include polyurethane. The material constituting the light absorbing member 170 may be a flexible material from the viewpoint of easy improvement of flexibility.

In the organic EL element 100, the light L1 from the light emitting layer 110 is transmitted through the light transmissive electrode 130 and is selectively reflected by the reflection filter 160. In this case, by using a reflection filter that selectively reflects a light component having a desired wavelength, as the reflection filter 160, it is possible to emit a light component (the reflected light L2) having a narrowed spectral width from the organic EL element 100. In addition, by adjusting the light emission direction of the light emitting layer 110, the relative position between the light emitting layer 110 and the reflection filter 160, the reflection position and the reflection angle of the reflection filter 160, and the like, the reflected light L2 reflected by the reflection filter 160 can be allowed to be emitted in a desired emission direction, so that it is possible to achieve various optical layouts.

In the organic EL element 100, a polymer filter may be used as the reflection filter 160, and for example, a filter having a resin layer having a microphase separation structure containing a block copolymer and including a lamellar-shaped micro domain may be used. In a case where a polymer filter is used, the organic EL element 100 is easily increased in area and improved in flexibility.

In the organic EL element 100, the light shielding electrode 120 may be a light reflective electrode. As a result, even in a case where the light emitting layer 110 emits light in the arrangement direction of the light shielding electrode 120, the light emitted in the arrangement direction of the light shielding electrode 120 is reflected by the light shielding electrode 120 to be allowed to travel in the arrangement direction of the reflection filter 160. In this case, high light utilization efficiency and high light emission intensity can be easily obtained.

The organic EL element 100 includes the light absorbing member 170, and the light absorbing member 170 can absorb the light component transmitted through the reflection filter 160 among the lights L1 from the light emitting layer 110. In this case, it is possible to suppress performance degradation (for example, a phenomenon that prevents the narrowing of the spectral width due to reflection, scattering, or the like of the transmitted light in the measurement apparatus) caused by the transmitted light that has been transmitted through the reflection filter 160.

The organic EL element 100 includes the light transmissive substrate 150. In this case, since a sufficient optical path length can be ensured, it is easy to reflect a lot of lights.

Figure 4A:
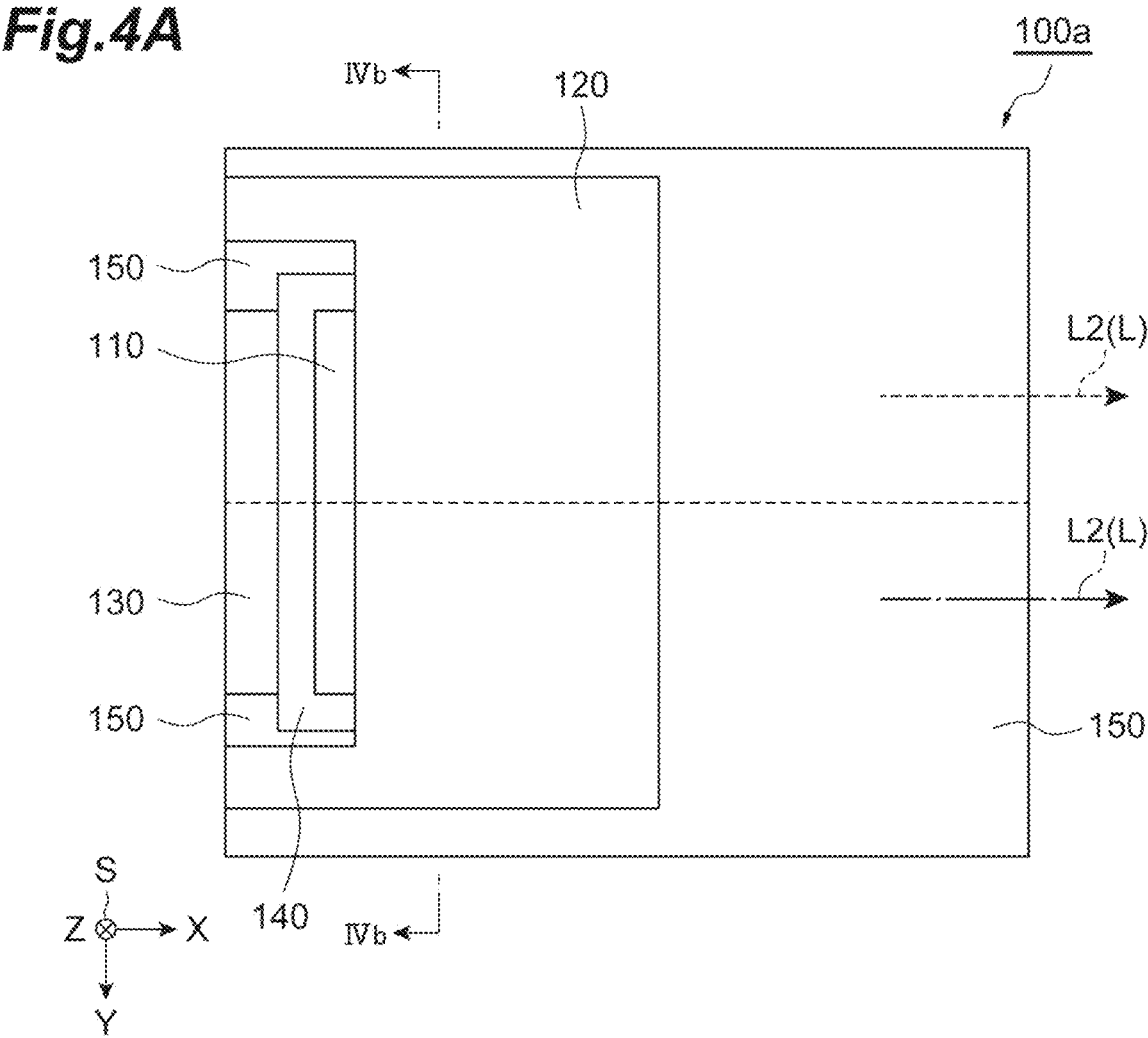
FIG. 4A is a schematic plan view illustrating an organic electroluminescent element of a second embodiment.
Figure 4B:
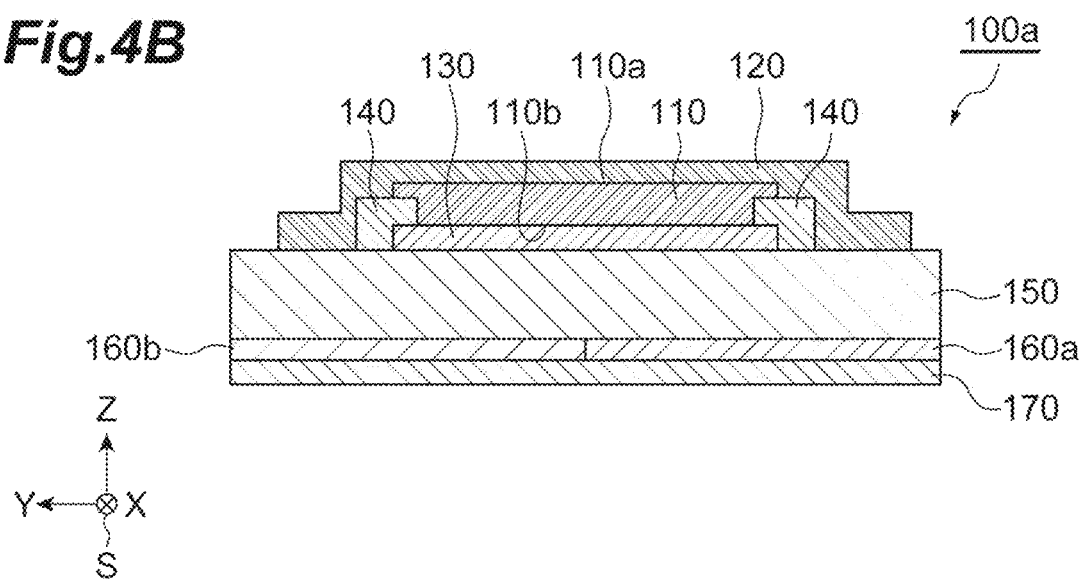
FIG. 4B is a cross-sectional view taken along line IVb-IVb in FIG. 4A.

FIG. 4A is a schematic plan view illustrating an organic EL element of a second embodiment, and FIG. 4B is a cross-sectional view taken along line IVb-IVb in FIG. 4A. An organic EL element 100a in FIG. 4A and FIG. 4B has the same configuration as the organic EL element 100 except that reflection filters 160a and 160b are provided instead of the reflection filter 160. That is, the organic EL element 100a includes a plurality of the reflection filters. The reflection filters 160a and 160b are reflection filters that are different from each other, and the wavelengths, the reflection angles (light emission directions; the same will be applied hereinafter), and the like of the reflected lights L2 reflected by the respective reflection filters 160a and 160b are different from each other. A plurality of the lights emitted from a plurality of the portions of the light emitting layer 110 are reflected at different positions (the reflection filters 160a and 160b).

As the reflection filters 160a and 160b, the above-described filters that can be used as the reflection filter 160 can be used. The reflection filters 160a and 160b have a rectangular shape in the XY plane. The reflection filters 160a and 160b have approximately half the size of the organic EL element 100a in the XY plane and are adjacent to each other in the Y-axis direction.

In the organic EL element 100a, the organic EL element 100a includes the reflection filters 160a and 160b selectively reflecting the lights L1 from the light emitting layer 110, so that it is possible to achieve various optical layouts while narrowing the spectral width. In addition, in the organic EL element 100a, the wavelength, the reflection angle, and the like of the reflected lights L2 are adjusted by using the reflection filters 160a and 160b as a plurality of the reflection filters, so that it is easy to achieve various optical layouts.

Figure 5:
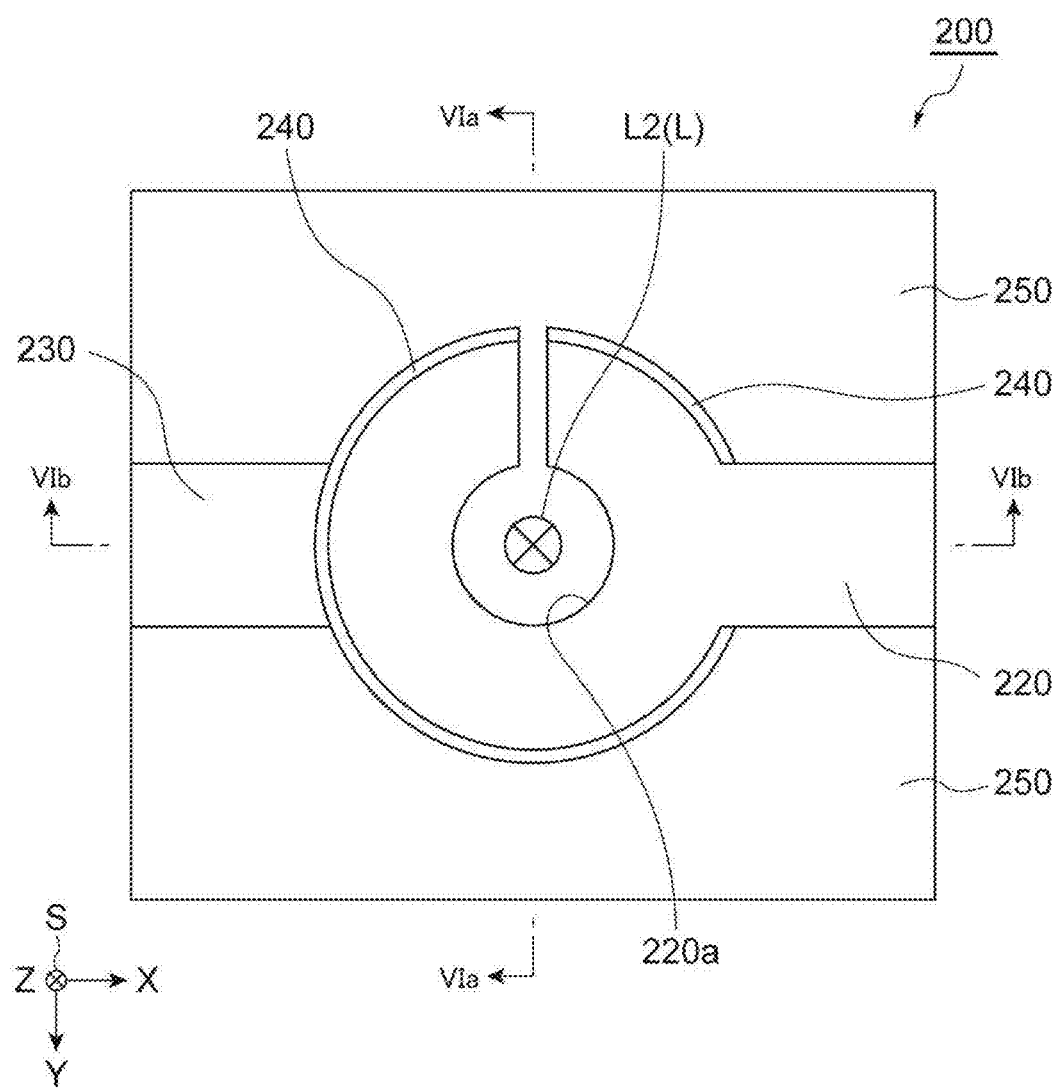
FIG. 5 is a schematic plan view illustrating an organic electroluminescent element of a third embodiment.
Figure 6A:
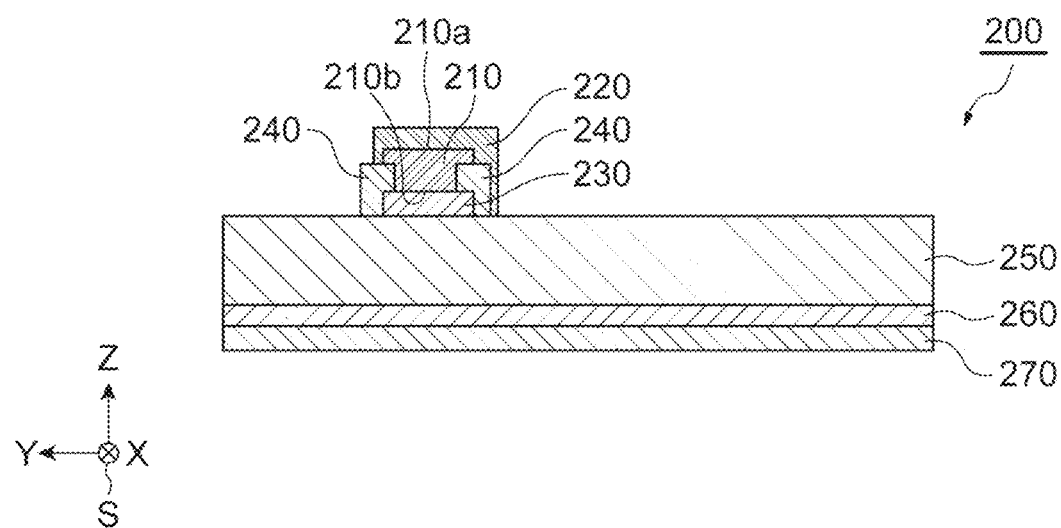
FIG. 6A is a cross-sectional view taken along line VIa-VIa in FIG. 5.
Figure 6B:
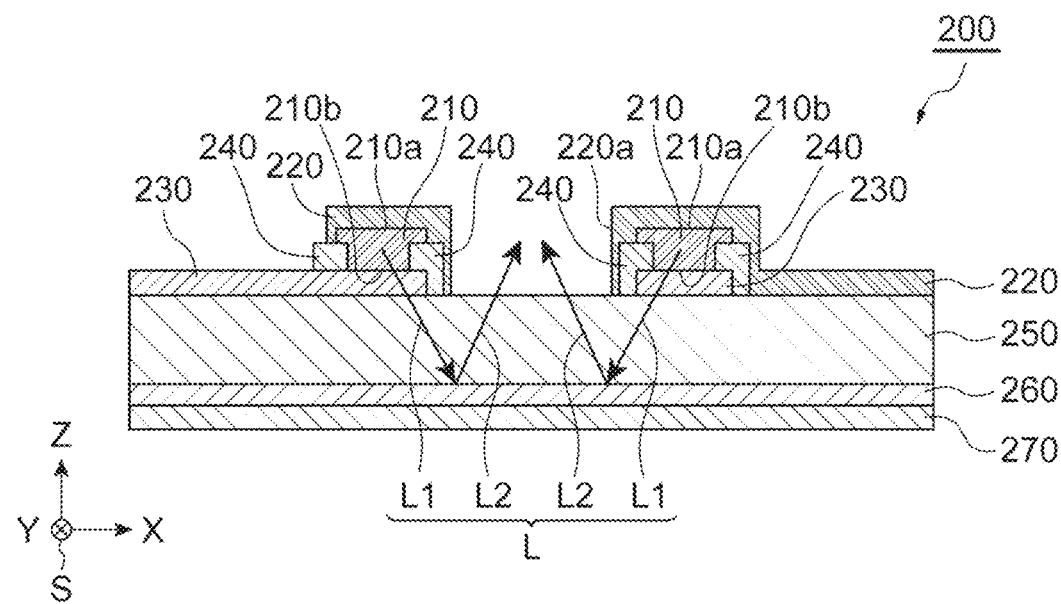
FIG. 6B is a cross-sectional view taken along line VIb-VIb in FIG. 5.

FIG. 5 is a schematic plan view illustrating an organic EL element of a third embodiment. FIG. 6A is a cross-sectional view taken along line VIa-VIa in FIG. 5, and FIG. 6B is a cross-sectional view taken along line VIb-VIb in FIG. 5. An organic EL element 200 in FIG. 5, FIG. 6A and FIG. 6B includes a light transmissive substrate 250, a reflection filter 260, and a light absorbing member 270 which are similar to the light transmissive substrate 150, the reflection filter 160, and the light absorbing member 170 of the organic EL element 100, and the configuration on the light transmissive substrate 250 is different from that of the organic EL element 100. The organic EL element 200 has a light emission opening that opens in the Z-axis direction at the center of the XY plane.

The organic EL element 200 includes a light emitting layer 210, a light shielding electrode (first electrode having a light shielding property) 220, a light transmissive electrode (second electrode having a light transmitting property) 230, and an insulating layer 240. The light absorbing member 270, the reflection filter 260, the light transmissive substrate 250, the light transmissive electrode 230, the light emitting layer 210, and a portion of the light shielding electrode 220 are laminated in this order. In the light emitting layer 210, the light shielding electrode 220, the light transmissive electrode 230, and the insulating layer 240, other configurations such as constituent materials and optical characteristics except for the shape and the arrangement may be the same as the light emitting layer 110, the light shielding electrode 120, the light transmissive electrode 130, and the insulating layer 140 of the organic EL element 100.

The light emitting layer 210 is arranged between the light shielding electrode 220 and the light transmissive electrode 230. The light emitting layer 210 has an annular shape in which a portion on the negative Y-axis direction side is split in the XY plane. The light emitting layer 210 is arranged so as to surround the light emission opening at the center of the organic EL element 200. The light emitting layer 210 has an opening through which the reflected lights L2 reflected by the reflection filter 260 are emitted, as an opening constituting a light emission opening. The light emitting layer 210 has one surface 210a and the other surface 210b facing each other in the Z-axis direction. The light emitting layer 210 emits lights L1 in the arrangement direction of the reflection filter 260 with respect to the light emitting layer 210 and irradiates the reflection filter 260 with the lights L1. In the organic EL element 200, a plurality of the reflected lights L2 reflected by the reflection filter 260 after being emitted from a plurality of portions of the light emitting layer 210 are emitted from the same portion of the light emission opening. A plurality of the lights L1 emitted from a plurality of the portions of the light emitting layer 210 are reflected at different positions of the reflection filter 260.

The light shielding electrode 220 is arranged on the one surface 210a side of the light emitting layer 210 and is in contact with the light emitting layer 210. More specifically, the light shielding electrode 220 includes a first electrode portion which is arranged on the one surface 210a side of the light emitting layer 210 and has a split annular shape similarly to the light emitting layer 210, second electrode portions which are arranged on the respective inner and outer peripheral sides of the light emitting layer 210 on the light transmissive substrate 250 and connected to the inner and outer peripheral sides of the first electrode portion, and a third electrode portion which extends in the X-axis direction from the end portion of the second electrode portion in the positive X-axis direction. The light shielding electrode 220 has an opening 220a through which the reflected light L2 reflected by the reflection filter 260 is emitted, as an opening constituting a light emission opening in the first electrode portion. At least one kind selected from the group consisting of the light emitting layer 210 and the light transmissive electrode 230 (in the present embodiment, the light emitting layer 210 and the light transmissive electrode 230) is not arranged in the opening 220a, and the reflected light L2 reflected by the reflection filter 260 is emitted from the opening 220a without being transmitted through the light emitting layer 210 and the light transmissive electrode 230. The second electrode portion is arranged between the light emitting layer 210 and the light emission opening, so that the light that is not irradiated on the reflection filter 260 is suppressed from being emitted to the outside of the organic EL element 200.

The light transmissive electrode 230 is arranged on the other surface 210b side of the light emitting layer 210 and is in contact with the light emitting layer 210. The light transmissive electrode 230 is arranged on the light transmissive substrate 250 and is in contact with the light transmissive substrate 250. The light transmissive electrode 230 includes a first electrode portion having a split annular shape similarly to the light emitting layer 210 and a second electrode portion which extends in the X-axis direction from the end portion of the first electrode portion in the negative X-axis direction. The light transmissive electrode 230 has an opening through which the reflected light L2 reflected by the reflection filter 260 is emitted, as an opening constituting the light emission opening in the first electrode portion.

The insulating layer 240 has a split annular shape similarly to the light emitting layer 210. The insulating layer 240 is arranged on the respective inner and outer peripheral sides of the light emitting layer 210.

In the organic EL element 200, the organic EL element 200 includes the reflection filter 260 selectively reflecting the lights L1 from the light emitting layer 210, so that it is possible to achieve various optical layouts while narrowing the spectral width. In addition, in the organic EL element 200, a plurality of the reflected lights L2 reflected by the reflection filter 260 after being emitted from a plurality of portions of the light emitting layer 210 are emitted from the same portion of the light emission opening, so that high light utilization efficiency and high light emission intensity can be easily obtained.

In the organic EL element 200, at least one kind selected from the group consisting of the light emitting layer 210 and the light transmissive electrode 230 is not arranged in the opening 220a, and the reflected light L2 reflected by the reflection filter 260 is emitted from the opening 220a without being transmitted through the light emitting layer 210 and the light transmissive electrode 230. Therefore, high light utilization efficiency and high light emission intensity can be easily obtained.

Figure 7:
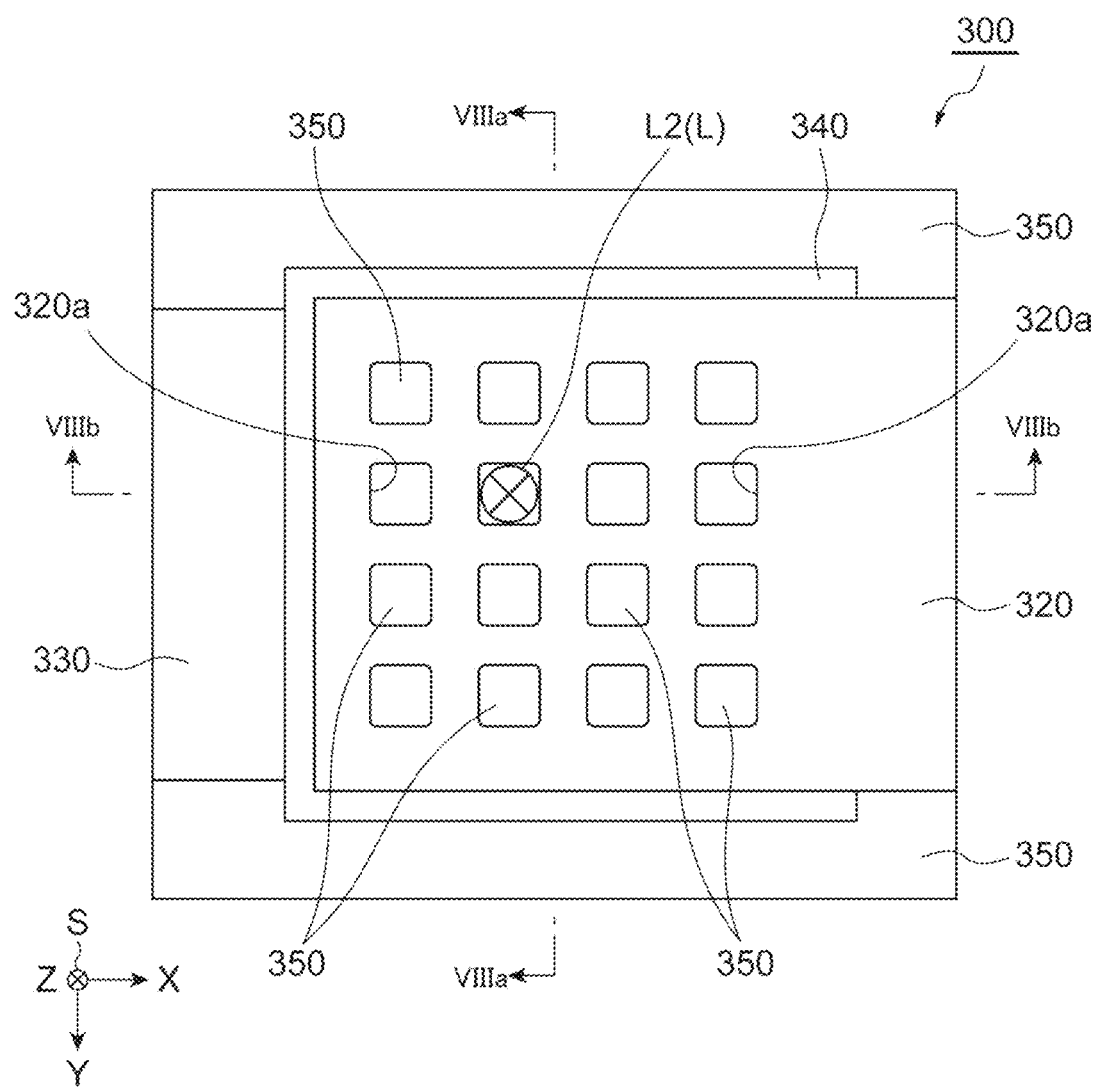
FIG. 7 is a schematic plan view illustrating an organic electroluminescent element of a fourth embodiment.
Figure 8A:
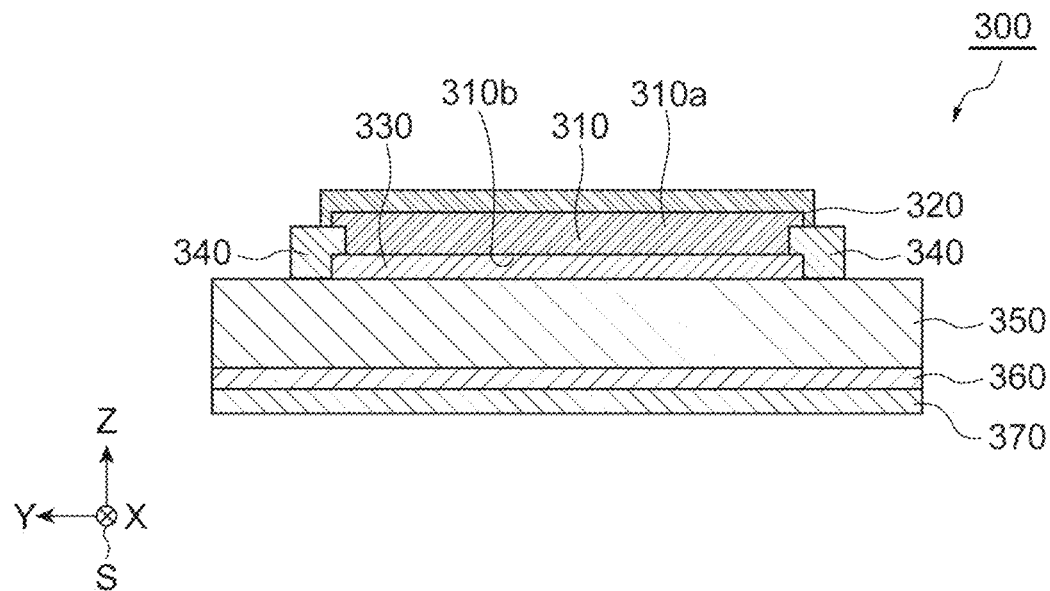
FIG. 8A is a cross-sectional view taken along line VIIIa-VIIIa in FIG. 7.
Figure 8B:
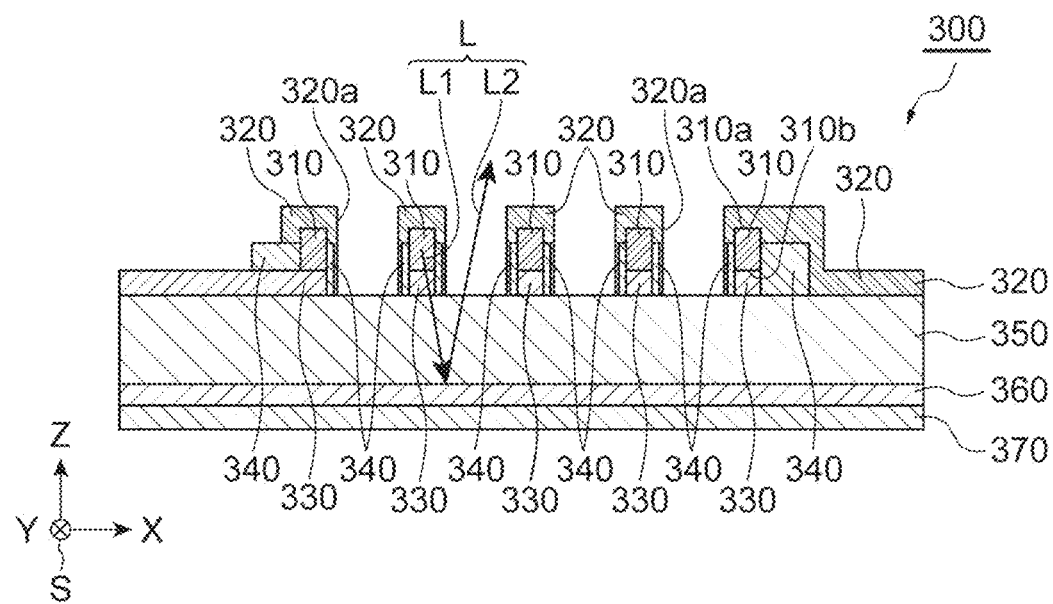
FIG. 8B is a cross-sectional view taken along line VIIIb-VIIIb in FIG. 7.

FIG. 7 is a schematic plan view illustrating an organic EL element of a fourth embodiment. FIG. 8A is a cross-sectional view taken along line VIIIa-VIIIa in FIG. 7, and FIG. 8B is a cross-sectional view taken along line VIIIb-VIIIb in FIG. 7. An organic EL element 300 in FIG. 7, FIG. 8A and FIG. 8B includes a light transmissive substrate 350, a reflection filter 360, and a light absorbing member 370 which are similar to the light transmissive substrate 150, the reflection filter 160, and the light absorbing member 170 of the organic EL element 100, and the configuration on the light transmissive substrate 350 is different from that of the organic EL element 100. The organic EL element 300 has a plurality of light emission openings and, specifically, has a plurality of the light emission openings that open in the Z-axis direction in the central region of the XY plane. The plurality of light emission openings are arranged in a 4×4 array shape. In FIG. 7, for the convenience, although the reflected light L2 is illustrated as being emitted from one light emission opening, the reflected light L2 may be emitted from another light emission opening, or the reflected light L2 may be emitted from all the light emission openings.

The organic EL element 300 includes a light emitting layer 310, a light shielding electrode (first electrode having a light shielding property) 320, a light transmissive electrode (second electrode having a light transmitting property) 330, and an insulating layer 340. The light absorbing member 370, the reflection filter 360, the light transmissive substrate 350, the light transmissive electrode 330, the light emitting layer 310, and a portion of the light shielding electrode 320 are laminated in this order. In the light emitting layer 310, the light shielding electrode 320, the light transmissive electrode 330, and the insulating layer 340, other configurations such as constituent materials and optical characteristics except for the shape and the arrangement may be the same as the light emitting layer 110, the light shielding electrode 120, the light transmissive electrode 130, and the insulating layer 140 of the organic EL element 100.

The light emitting layer 310 is arranged between the light shielding electrode 320 and the light transmissive electrode 330. The light emitting layer 310 has a lattice shape in the XY plane. The light emitting layer 310 is arranged in the central region of the organic EL element 300 in the XY plane, and the lattice-shaped gap is configured as the light emission opening. The light emitting layer 310 has one surface 310a and the other surface 310b facing each other in the Z-axis direction. The light emitting layer 310 emits the lights L1 in the arrangement direction of the reflection filter 360 with respect to the light emitting layer 310 and irradiates the reflection filter 360 with the lights L1. In the organic EL element 300, the reflected lights L2 reflected by the reflection filter 360 after being emitted from the light emitting layer 310 are emitted from any one of the light emission openings.

The light shielding electrode 320 is arranged on the one surface 310a side of the light emitting layer 310 and is in contact with the light emitting layer 310. More specifically, the light shielding electrode 320 includes a first electrode portion having a lattice shape which is arranged on the one surface 310a side of the light emitting layer 310, a second electrode portion which is arranged along the inner wall of the light emission opening and connected to the first electrode portion, and a third electrode portion which extends in the X-axis direction from the end portion of the first electrode portion in the positive X-axis direction. The light shielding electrode 320 has an opening 320a through which the reflected light L2 reflected by the reflection filter 360 is emitted, as an opening constituting the light emission opening in the first electrode portion, and has a plurality of the openings 320a. At least one kind selected from the group consisting of the light emitting layer 310 and the light transmissive electrode 330 (in the present embodiment, the light emitting layer 310 and the light transmissive electrode 330) is not arranged in the opening 320a, and the reflected light L2 reflected by the reflection filter 360 is emitted from the opening 320a without being transmitted through the light emitting layer 310 and the light transmissive electrode 330. The second electrode portion is arranged between the light emitting layer 310 and the light emission opening, so that the light that is not irradiated on the reflection filter 360 is suppressed from being emitted to the outside of the organic EL element 300.

The light transmissive electrode 330 is arranged on the other surface 310b side of the light emitting layer 310 and is in contact with the light emitting layer 310. The light transmissive electrode 330 is arranged on the light transmissive substrate 350 and is in contact with the light transmissive substrate 350. The light transmissive electrode 330 includes a first electrode portion having a lattice shape which is arranged on the other surface 310b side of the light emitting layer 310 and a second electrode portion which extends in the X-axis direction from the end portion of the first electrode portion in the negative X-axis direction.

The insulating layer 340 includes a portion arranged between the second electrode portion of the light shielding electrode 320 and the first electrode portion of the light transmissive electrode 330 and a portion arranged on the outer peripheral side of the light emitting layer 310.

In the organic EL element 300, the organic EL element 300 includes the reflection filter 360 selectively reflecting the lights L1 from the light emitting layer 310, so that it is possible to achieve various optical layouts while narrowing the spectral width. In addition, since the organic EL element 300 has a plurality of light emission openings, the light is adjusted so as to be emitted from a desired light emission opening by adjusting the reflection angle of a plurality of the reflected lights L2 reflected by the reflection filter 360 after being emitted from a plurality of the portions of the light emitting layer 310, so that it is easy to achieve various optical layouts. In the organic EL element 300, at least one kind selected from the group consisting of the light emitting layer 310 and the light transmissive electrode 330 is not arranged in the opening 320a, and the reflected light L2 reflected by the reflection filter 360 is emitted from the opening 320a without being transmitted through the light emitting layer 310 and the light transmissive electrode 330. Therefore, high light utilization efficiency and high light emission intensity can be easily obtained.

Figure 9:
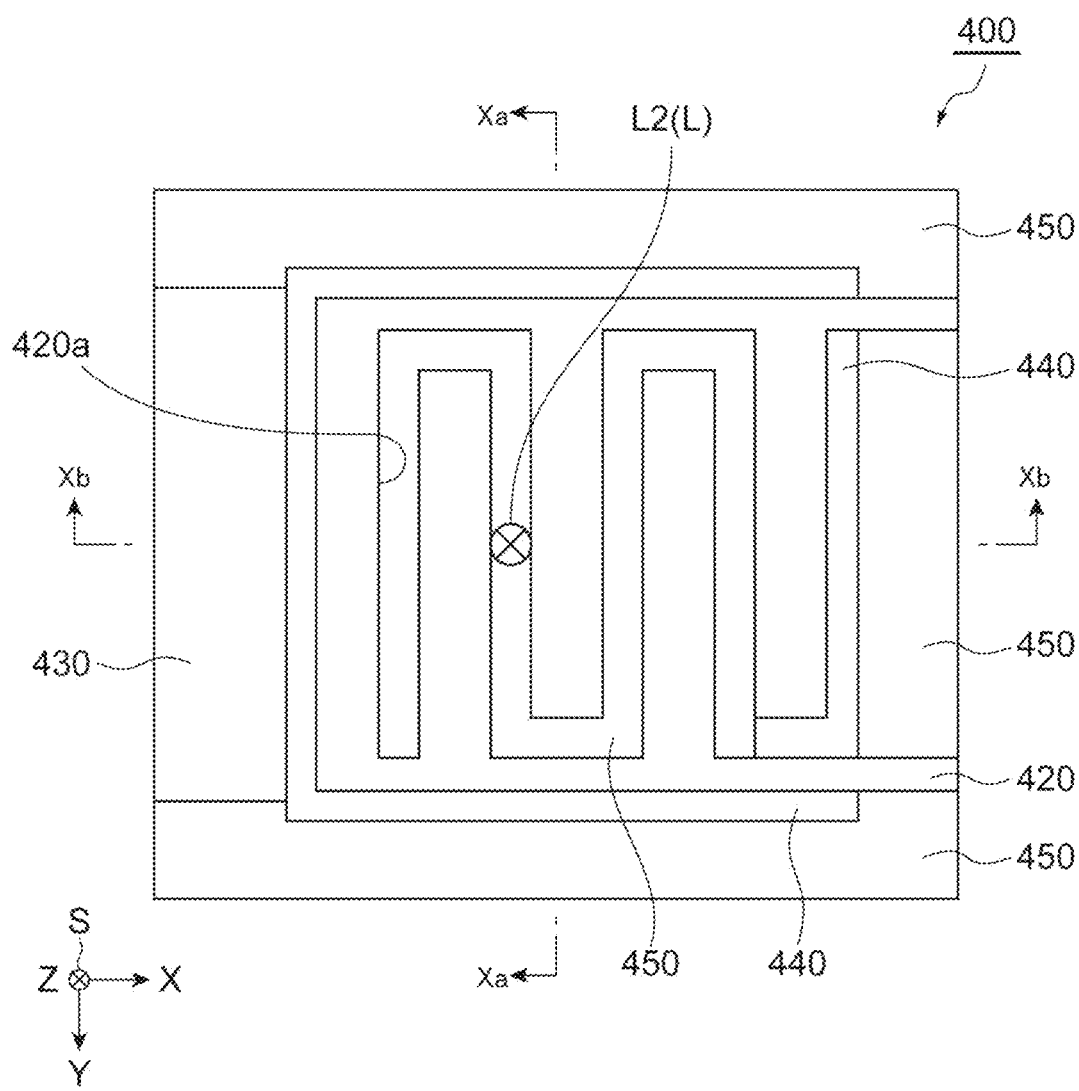
FIG. 9 is a schematic plan view illustrating an organic electroluminescent element of a fifth embodiment.
Figure 10A:
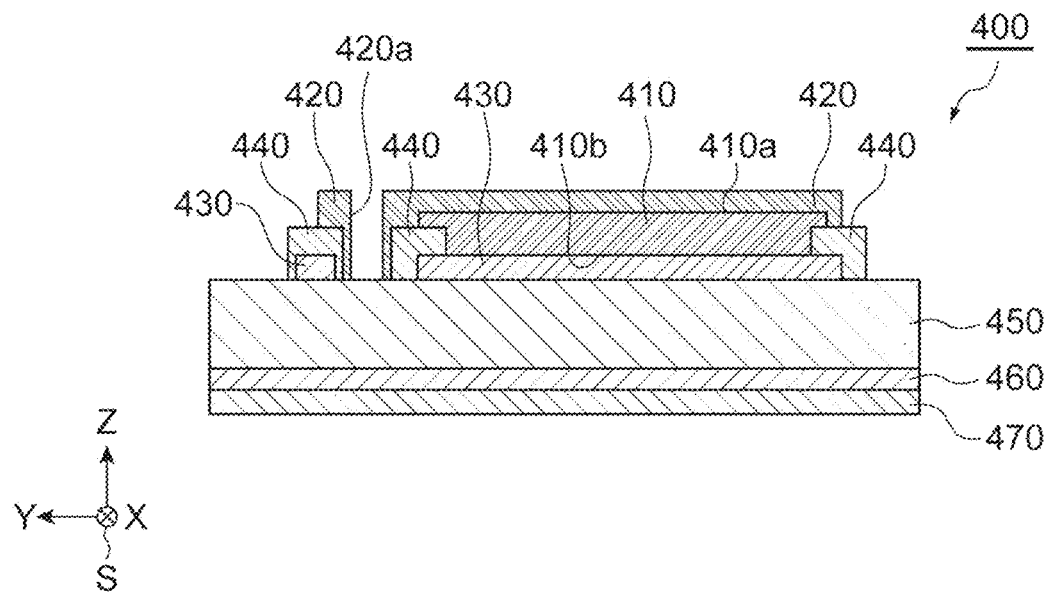
FIG. 10A is a cross-sectional view taken along line Xa-Xa in FIG. 9.
Figure 10B:
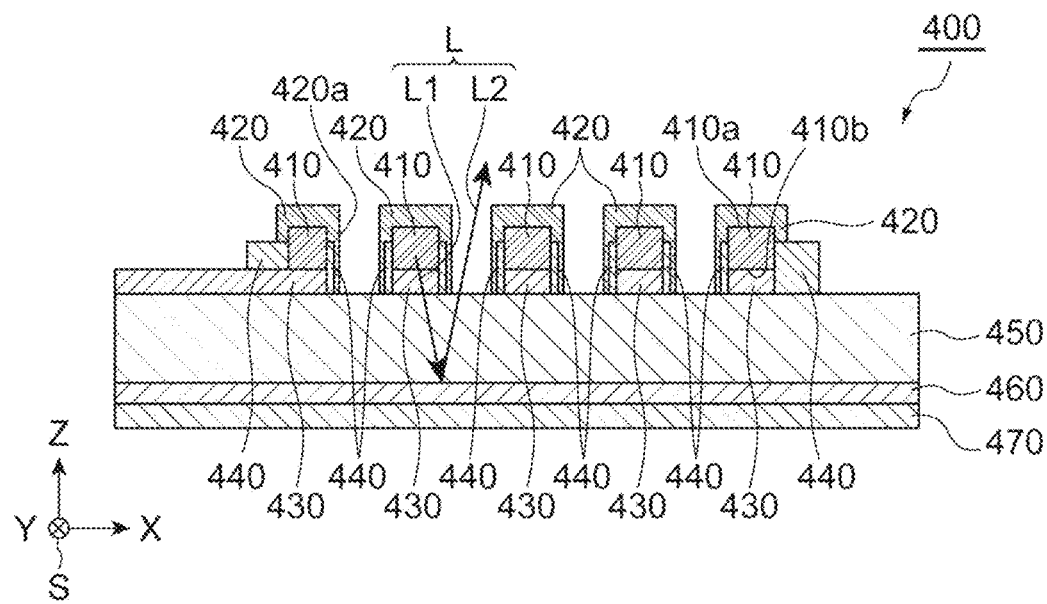
FIG. 10B is a cross-sectional view taken along line Xb-Xb in FIG. 9.

FIG. 9 is a schematic plan view illustrating an organic EL element of a fifth embodiment. FIG. 10A is a cross-sectional view taken along line Xa-Xa in FIG. 9, and FIG. 10B is a cross-sectional view taken along line Xb-Xb in FIG. 9. The organic EL element 400 in FIG. 9, FIG. 10A and FIG. 10B includes a light transmissive substrate 450, a reflection filter 460, and a light absorbing member 470 which are similar to the light transmissive substrate 150, the reflection filter 160, and the light absorbing member 170 of the organic EL element 100, and the configuration on the light transmissive substrate 450 is different from that of the organic EL element 100. The organic EL element 400 has a light emission opening that opens in the Z-axis direction in the central region of the XY plane. In FIG. 9, for the convenience, although the reflected light L2 is illustrated as being emitted from one place of the light emission opening, the reflected light L2 may be emitted from another place of the light emission opening, and the reflected light L2 may be emitted from the entire light emission opening.

The organic EL element 400 includes a light emitting layer 410, a light shielding electrode (first electrode having a light shielding property) 420, a light transmissive electrode (second electrode having a light transmitting property) 430, and an insulating layer 440. The light absorbing member 470, the reflection filter 460, the light transmissive substrate 450, the light transmissive electrode 430, the light emitting layer 410, and a portion of the light shielding electrode 420 are laminated in this order. In the light emitting layer 410, the light shielding electrode 420, the light transmissive electrode 430, and the insulating layer 440, other configurations such as constituent materials and optical characteristics except for the shape and the arrangement may be the same as the light emitting layer 110, the light shielding electrode 120, the light transmissive electrode 130, and the insulating layer 140 of the organic EL element 100.

The light emitting layer 410 is arranged between the light shielding electrode 420 and the light transmissive electrode 430. The light emitting layer 410 is composed of five elongated portions extending in the Y-axis direction, and the elongated portions are arranged in the X-axis direction through the light emission opening. The light emitting layer 410 has one surface 410a and the other surface 410b facing each other in the Z-axis direction. The light emitting layer 410 emits the light L1 in the arrangement direction of the reflection filter 460 with respect to the light emitting layer 410 and irradiates the reflection filter 460 with the light L1. In the organic EL element 400, the reflected light L2 reflected by the reflection filter 460 after being emitted from the light emitting layer 410 is emitted from any place of the light emission opening.

The light shielding electrode 420 is arranged on the one surface 410a side of the light emitting layer 410 and is in contact with the light emitting layer 410. More specifically, the light shielding electrode 420 includes five elongated first electrode portions which are arranged on the one surface 410a side of the light emitting layer 410 along the arrangement position of the light emitting layer 410, a second electrode portion which is arranged along the inner wall of the light emission opening and connected to the first electrode portion, and a pair of third electrode portions which extend in the X-axis direction perpendicular to the extending direction of the first electrode portion. The five first electrode portions are alternately connected to one third electrode portion and the other third electrode portion. That is, the light shielding electrode 420 has a structure in which the comb portion of one electrode and the comb portion of the other electrode of two comb-shaped electrodes are alternately arranged in the X-axis direction and the two comb-shaped electrodes are connected to each other at the end portion in the negative X-axis direction. The light emission opening is formed between two comb-shaped electrodes, and the light shielding electrode 420 has an opening 420a as an opening constituting the light emission opening. At least one kind selected from the group consisting of the light emitting layer 410 and the light transmissive electrode 430 (in the present embodiment, the light emitting layer 410 and the light transmissive electrode 430) is not arranged in the opening 420a, and the reflected light L2 reflected by the reflection filter 460 is emitted from the opening 420a without being transmitted through the light emitting layer 410 and the light transmissive electrode 430. The second electrode portion is arranged between the light emitting layer 410 and the light emission opening, so that the light that is not irradiated on the reflection filter 460 is suppressed from being emitted to the outside of the organic EL element 400.

The light transmissive electrode 430 is arranged on the other surface 410b side of the light emitting layer 410 and is in contact with the light emitting layer 410. The light transmissive electrode 430 is arranged on the light transmissive substrate 450 and is in contact with the light transmissive substrate 450. The light transmissive electrode 430 includes five elongated first electrode portions which are arranged on the other surface 410b side of the light emitting layer 410 along the arrangement position of the light emitting layer 410 and a second electrode portion which extends in the X-axis direction from the electrode portion arranged on the most negative X-axis direction side among the five first electrode portions.

The insulating layer 440 includes a portion arranged between the second electrode portion of the light shielding electrode 420 and the first electrode portion of the light transmissive electrode 430 and a portion arranged on the outer peripheral side of the region in which five elongated portions of the light emitting layer 410 are arranged.

In the organic EL element 400, since the organic EL element 400 includes the reflection filter 460 selectively reflecting the lights L1 from the light emitting layer 410, it is possible to achieve various optical layouts while narrowing the spectral width.

In the organic EL element 400, since the light emitting layer 410 includes a plurality of portions, it is easy to achieve various optical layouts by driving only desired portions. In addition, in the organic EL element 400, at least one kind selected from the group consisting of the light emitting layer 410 and the light transmissive electrode 430 is not arranged in the opening 420a, and the reflected light L2 reflected by the reflection filter 460 is emitted from the opening 420a without being transmitted through the light emitting layer 410 and the light transmissive electrode 430. Therefore, high light utilization efficiency and high light emission intensity can be easily obtained.

Figure 11:
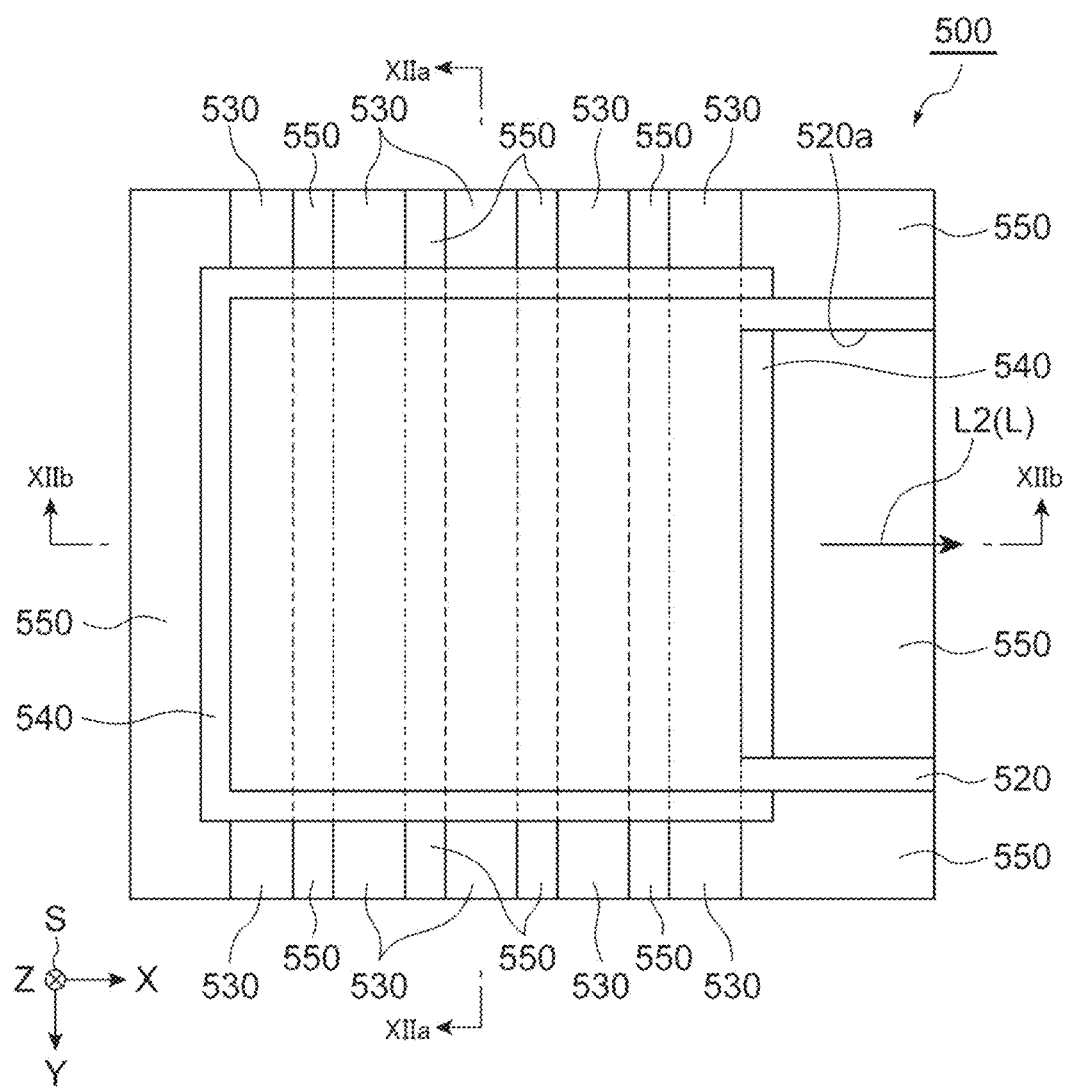
FIG. 11 is a schematic plan view illustrating an organic electroluminescent element of a sixth embodiment.
Figure 12A:
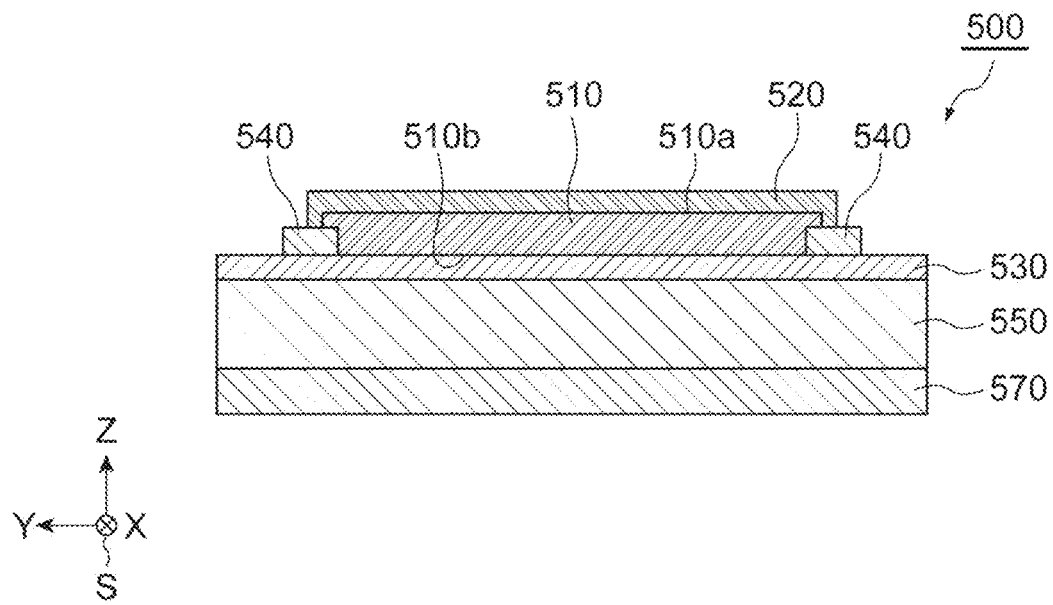
FIG. 12A is a cross-sectional view taken along line XIIa-XIIa in FIG. 11.

FIG. 11 is a schematic plan view illustrating an organic EL element of a sixth embodiment. FIG. 12A is a cross-sectional view taken along line XIIa-XIIa in FIG. 11, and FIG. 12B is a cross-sectional view taken along line XIIb-XIIb in FIG. 11.

Figure 12B:
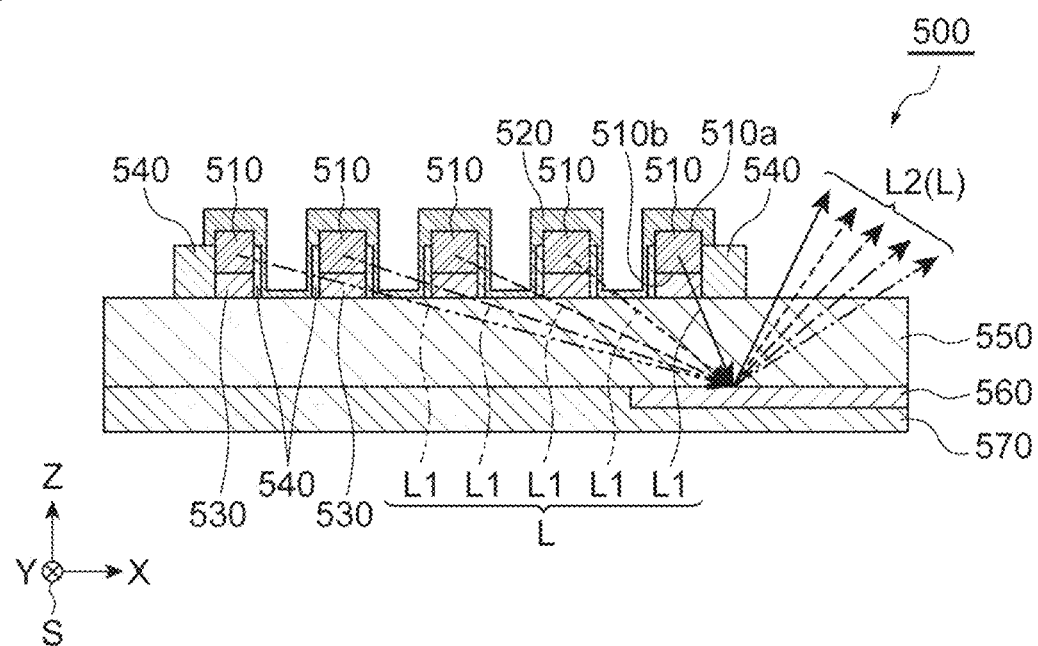
FIG. 12B is a cross-sectional view taken along line XIIb-XIIb in FIG. 11.

An organic EL element 500 in FIG. 11, FIG. 12A and FIG. 12B includes a light emitting layer 510, a light shielding electrode 520, a light transmissive electrode 530, an insulating layer 540, a light transmissive substrate 550, a reflection filter 560, and a light absorbing member 570. The light transmissive substrate 550 has the same configuration as the light transmissive substrate 150 of the organic EL element 100. In the light emitting layer 510, the light shielding electrode 520, the light transmissive electrode 530, the insulating layer 540, the reflection filter 560, and the light absorbing member 570, other configurations such as constituent materials and optical characteristics except for the shape and the arrangement may be the same as the light emitting layer 110, the light shielding electrode 120, the light transmissive electrode 130, the insulating layer 140, the reflection filter 160, and the light absorbing member 170 of the organic EL element 100.

The light emitting layer 510 is arranged between the light shielding electrode 520 and the light transmissive electrode 530. The light emitting layer 510 is composed of five elongated portions extending in the Y-axis direction, and the elongated portions are arranged in the X-axis direction. The light emitting layer 510 has one surface 510a and the other surface 510b facing each other in the Z-axis direction.

The light shielding electrode 520 is arranged on the one surface 510a side of the light emitting layer 510 and is in contact with the light emitting layer 510. More specifically, the light shielding electrode 520 includes five elongated first electrode portions which are arranged on the one surface 510a side of the light emitting layer 510 along the arrangement position of the light emitting layer 510, a second electrode portion which is arranged along the inner wall between the first electrode portions and connected to the first electrode portions, and a third electrode portion which is arranged at the bottom portion between the first electrode portions and connected to the second electrode portion. The second electrode portion is arranged around the light emitting layer 510, so that the light that is not irradiated on the reflection filter 560 is suppressed from being emitted to the outside of the organic EL element 500.

The organic EL element 500 has a light emission opening that opens in the Z-axis direction at the end portion in the positive X-axis direction, and the light shielding electrode 520 has an opening 520a as an opening constituting the light emission opening. At least one kind selected from the group consisting of the light emitting layer 510 and the light transmissive electrode 530 (in the present embodiment, the light emitting layer 510 and the light transmissive electrode 530) is not arranged in the opening 520a, and the reflected light L2 reflected by the reflection filter 560 is emitted from the opening 520a without being transmitted through the light emitting layer 510 and the light transmissive electrode 530.

The light transmissive electrode 530 is arranged on the other surface 510b side of the light emitting layer 510 and is in contact with the light emitting layer 510. The light transmissive electrode 530 is arranged on the light transmissive substrate 550 and is in contact with the light transmissive substrate 550. The light transmissive electrode 530 is composed of five elongated members which extend from one end to the other end of the organic EL element 500 in the Y-axis direction along the arrangement position of the light emitting layer 510.

The insulating layer 540 includes a portion arranged between the second electrode portion of the light shielding electrode 520 and the light transmissive electrode 530 and a portion arranged on the outer peripheral side of the region where the light emitting layer 510 is arranged.

The light absorbing member 570 has a rectangular recess in the XY plane near the end portion of the organic EL element 500 on the positive X-axis direction side, and the reflection filter 560 is arranged in the recess.

In the organic EL element 500, the same place of the reflection filter 560 is irradiated with a plurality of lights L1 emitted from a plurality of portions of the light emitting layer 510, and a plurality of reflected lights L2 reflected at the same place are emitted. A plurality of the reflected lights L2 have different reflection angles. The wavelengths of a plurality of the reflected lights L2 may be the same as each other or may be different from each other.

In the organic EL element 500, since the organic EL element 500 includes the reflection filter 560 selectively reflecting the lights L1 from the light emitting layer 510, it is possible to achieve various optical layouts while narrowing the spectral width. In addition, in the organic EL element 500, since a plurality of the reflected lights L2 reflected at the same place of the reflection filter 560 are emitted, it is easy to achieve various optical layouts by adjusting the reflection angle of the reflected light L2.

In the organic EL element 500, since the light emitting layer 510 includes a plurality of portions, it is easy to achieve various optical layouts by driving only desired portions. In addition, in the organic EL element 500, at least one kind selected from the group consisting of the light emitting layer 510 and the light transmissive electrode 530 is not arranged in the opening 520a, and the reflected light L2 reflected by the reflection filter 560 is emitted from the opening 520a without being transmitted through the light emitting layer 510 and the light transmissive electrode 530. Therefore, high light utilization efficiency and high light emission intensity can be easily obtained.

A measurement apparatus (analyzing apparatus) of the present embodiment includes the above-described organic EL element and a light detector. The detector detects light (reflected light) emitted from the organic EL element. The light emitted from the organic EL element can contain near-infrared light, and for example, can contain a light component having a peak wavelength in the range of 400 to 2500 nm. In the measurement apparatus of the present embodiment, by using the above-described organic EL element, it is possible to achieve various optical layouts while narrowing the spectral width.

Examples of the measurement apparatus include a living body measurement apparatus. In the living body measurement apparatus, living body sensing can be performed by irradiating a living body with light (near-infrared light or the like) emitted from an organic EL element and measuring intensity change of light absorption, reflected light, scattered light, emitted light, or the like by living tissues.

The embodiments of the organic EL element and the living body measurement apparatus are not limited to the above-described embodiments, and various modifications are possible.

The organic EL element can be used not only as a light source of a measurement apparatus but also as a light source for optical communication, a light source for biometric authentication, a light source for a sensor, and the like. In the organic EL element, the emission position of the reflected light is not limited to the above-described positions. For example, in the organic EL element 200, the reflected light L2 is emitted from the light emission opening on the inner peripheral side of the light emitting layer 210, but the reflected light may be emitted from the outer peripheral side of the light emitting layer 210. The light from the light emitting layer may be further reflected by a light reflective member (a reflection filter or a member different from the reflection filter) after being reflected by the reflection filter.

The shape of each constituent member of the organic EL element is not limited to the above-described shape such as a rectangular shape or an annular shape, but the shape may be any shape such as a perfect circle shape, an elliptical shape, a polygonal shape, a rectangular annular shape, or a polygonal annular shape. For example, in the organic EL element 200, the first electrode portion of the light shielding electrode 220 has an annular shape with an opening, but the first electrode portion of the light shielding electrode 220 may have a circular shape without an opening. In the organic EL element 400, the elongated portions of the light emitting layer 410 may be connected to each other.

The light absorbing member is not limited to a layer-shaped member. The light absorbing member has a light absorbing portion located on the side opposite to the light emitting layer with respect to the reflection filter and may further include a light absorbing portion at another position. For example, the light absorbing member may be in a mode where the light absorbing member has an opening through which light reflected by the reflection filter is emitted and covers the entire area of the organic EL element other than the light absorbing member. In this case, since the entire area of the organic EL element other than the light absorbing member is covered by the portion excluding the opening, the light leaked from the organic EL element is reflected, scattered, or the like in the measurement apparatus, so that it is possible to suppress the phenomenon preventing the narrowing of the spectral width or the like.

The number of constituent members, light emission openings, and the like of the organic EL element is not limited to the number described above. For example, the light emitting layer may be a single light emitting layer or a plurality of light emitting layers. The light emission opening may be a single light emission opening or a plurality of light emission openings.

In the organic EL element, the light transmissive electrode and the reflection filter may be in contact with each other without a light transmissive substrate interposed between the light transmissive electrode and the reflection filter. In this case, the organic EL element can be thinned.

Figure 13:
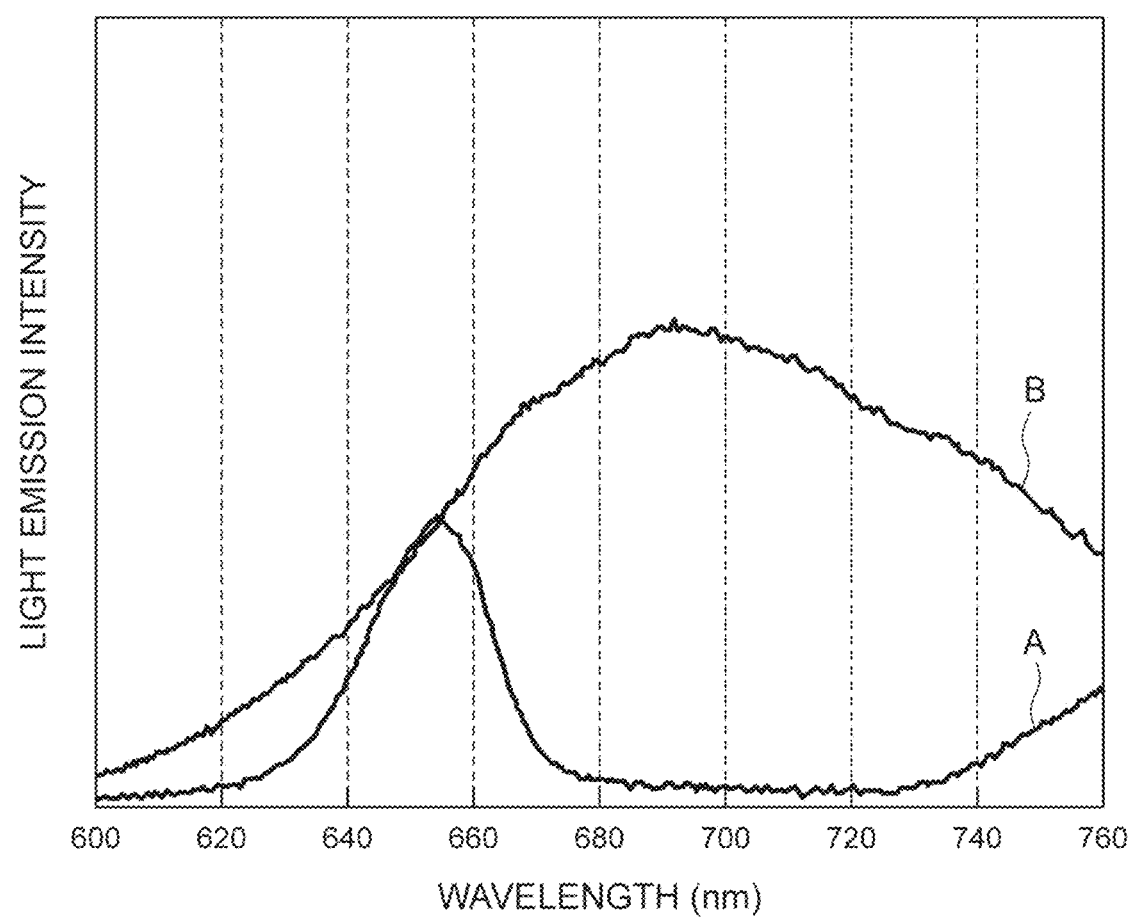
FIG. 13 is a drawing illustrating an example of an emission spectrum.

FIG. 13 is a drawing illustrating an example of an emission spectrum. Reference symbol A denotes an emission spectrum of a reflected light that travels in a direction inclined with respect to the main surface of the reflection filter 160 from the light emitting layer 110 in the organic EL element 100 and is reflected by the reflection filter 160. Reference symbol B denotes an emission spectrum (equivalent to the emission spectrum of the light emitted from the light emitting layer) of a reflected light that travels in a direction inclined with respect to the main surface of a mirror of an organic EL element having a structure in which the minor reflecting all the wavelengths is arranged instead of the reflection filter 160 and the light absorbing member 170 in the organic EL element 100 and is reflected by the mirror. According to FIG. 13, it is confirmed that, even in the case of the reflected light reflected by the reflection filter, the light emission intensity equivalent to the light emitted from the light emitting layer can be obtained. That is, it is possible to obtain high light utilization efficiency and high light emission intensity while achieving various optical layouts. In addition, the emission spectrum of the reference symbol A is an emission spectrum of the reflected light reflected after being irradiated on the reflection filter with a predetermined incidence angle, so that it is confirmed that the emission spectrum of the reference symbol A is detected at a position (peak position) different from that of the emission spectrum of the reference symbol B. For example, in the organic EL element, the peak wavelength of the light reflected by the reflection filter after being emitted from the light emitting layer may be smaller than the peak wavelength of the light after being emitted from the light emitting layer and before being reflected by the reflection filter. In this manner, in the organic EL element, the wavelength of the reflected light can be adjusted by adjusting the incidence angle.

In the organic EL element, the light emission direction of the light emitting layer, the relative position between the light emitting layer and the reflection filter, the reflection position and the reflection angle of the reflection filter, and the like can be adjusted so that the reflected light having a desired wavelength, reflection angle, and the like can be obtained. The organic EL element may be in a mode where the light reflected by the reflection filter after being emitted from the first portion of the light emitting layer and the light reflected by the reflection filter after being emitted from the second portion of the light emitting layer contain light components having different wavelengths or contain light components having the same wavelength. The organic EL element may be in a mode where a reflection angle of the light reflected by the reflection filter after being emitted from the first portion of the light emitting layer and a reflection angle of the light reflected by the reflection filter after being emitted from the second portion of the light emitting layer is different from each other or is the same each other. The organic EL element may be in a mode where the light reflected by the reflection filter after being emitted from the first portion of the light emitting layer and the light reflected by the reflection filter after being emitted from the second portion of the light emitting layer is emitted from the same portion in the same opening (for example, the opening of the light shielding electrode). The organic EL element may be in a mode where the light reflected by the reflection filter after being emitted from the first portion of the light emitting layer and the light reflected by the reflection filter after being emitted from the second portion of the light emitting layer are emitted from different portions of the same opening (for example, the opening of the light shielding electrode). The organic EL element may be in a mode where the same place of the reflection filter is irradiated with the light from the first portion of the light emitting layer and the light from the second portion of the light emitting layer.

A layer (for example, an organic layer) other than the light emitting layer may be further arranged between the light shielding electrode and the light transmissive electrode. Examples of such a layer include a hole transport layer, an electron transport layer, a hole injection layer, an electron injection layer, a hole blocking layer, an electron blocking layer, and an exciton blocking layer. Each of these layers may be a single layer or a plurality of layers.

The hole transport layer has a function of transporting holes. Examples of a hole transport material constituting the hole transport layer include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline based copolymer, a conductive polymer oligomer, and a thiophene oligomer.

The electron transport layer has a function of transporting electrons. Examples of an electron transport material constituting the electron transport layer include a nitro-substituted fluorene derivative, a diphenylquinone derivative, a thiopyrandioxide derivative, a carbodiimide, a fluorenylidenemethane derivative, anthraquinodimethane, anthrone derivative, and an oxadiazole derivative, or the like.

The hole injection layer can be arranged between the anode and the light emitting layer or between the anode and the hole transport layer in order to reduce the driving voltage, improve the light emission luminance, and the like. The electron injection layer can be arranged between the cathode and the light emitting layer or between the cathode and the electron transport layer in order to reduce the driving voltage, improve the light emission luminance, and the like.

The hole blocking layer can block holes from reaching the electron transport layer while transporting electrons. Therefore, it is easy to improve the probability of recombination of electrons and holes in the light emitting layer. The electron blocking layer can block electrons from reaching the hole transport layer while transporting holes. Therefore, it is easy to improve the probability of recombination of electrons and holes in the light emitting layer.

The exciton blocking layer can block excitons generated by recombination of holes and electrons in the light emitting layer from diffusing into the charge transport layers. Therefore, the excitons can be efficiently confined in the light emitting layer, and the light emission efficiency of the element can be easily improved.

REFERENCE SIGNS LIST 100, 100a, 200, 300, 400, 500: organic EL element, 110, 210, 310, 410, 510: light emitting layer, 110a, 210a, 310a, 410a, 510a: one surface, 110b, 210b, 310b, 410b, 510b: other surface, 120, 220, 320, 420, 520: light shielding electrode (first electrode), 220a, 320a, 420a, 520a: opening, 130, 230, 330, 430, 530: light transmissive electrode (second electrode), 160, 160a, 160b, 260, 360, 460, 560: reflection filter, 170, 270, 370, 470, 570: light absorbing member, L1: light.

What is claimed is:

1. An organic electroluminescent element comprising:
a light emitting layer containing an organic light emitting material;
a first electrode having a light shielding property, the first electrode being arranged on one surface side of the light emitting layer;
a second electrode having a light transmitting property, the second electrode being arranged on the other surface side of the light emitting layer; and
a reflection filter being arranged on a side opposite to the light emitting layer with respect to the second electrode and selectively reflecting light from the light emitting layer.

2. The organic electroluminescent element according to claim 1, further comprising a light absorbing member having a light absorbing portion located on a side opposite to the light emitting layer with respect to the reflection filter.

3. The organic electroluminescent element according to claim 2, wherein the light absorbing member has an opening through which light reflected by the reflection filter is emitted and covers an entire area of the organic electroluminescent element other than the light absorbing member.

4. The organic electroluminescent element according to claim 1, comprising a plurality of the reflection filter.

5. The organic electroluminescent element according to claim 1, wherein the reflection filter is a polymer filter.

6. The organic electroluminescent element according to claim 1, wherein the first electrode is a light reflective electrode.

7. The organic electroluminescent element according to claim 1, wherein the first electrode has an opening through which light reflected by the reflection filter is emitted.

8. The organic electroluminescent element according to claim 7, wherein the first electrode has a plurality of the opening.

9. The organic electroluminescent element according to claim 7, wherein a light reflected from the reflection filter after being emitted from a first portion of the light emitting layer and a light reflected from the reflection filter after being emitted from a second portion of the light emitting layer are emitted from a same portion of the opening.

10. The organic electroluminescent element according to claim 1, wherein a light reflected from the reflection filter after being emitted from a first portion of the light emitting layer and a light reflected from the reflection filter after being emitted from a second portion of the light emitting layer contain light components having different wavelengths.

11. The organic electroluminescent element according to claim 1, wherein a reflection angle of a light reflected from the reflection filter after being emitted from a first portion of the light emitting layer and a reflection angle of a light reflected from the reflection filter after being emitted from a second portion of the light emitting layer are different from each other.

12. The organic electroluminescent element according to claim 1, wherein a same place of the reflection filter is irradiated with a light from a first portion of the light emitting layer and a light from a second portion of the light emitting layer.

13. The organic electroluminescent element according to claim 1, further comprising a light transmissive substrate arranged between the second electrode and the reflection filter.

14. The organic electroluminescent element according to claim 1, wherein the second electrode and the reflection filter are in contact with each other.

15. A measurement apparatus comprising the organic electroluminescent element according to claim 1 and a light detector.

* * * * *